United States Patent [19]

Huang et al.

[11] Patent Number: 4,708,933
[45] Date of Patent: Nov. 24, 1987

[54] IMMUNOLIPOSOME ASSAY-METHODS AND PRODUCTS

[76] Inventors: Leaf Huang, 352 Dominion Cir., Knoxville, Tenn. 37922; Rodney J. Y. Ho, 1611 Laurel Ave., Knoxville, Tenn. 37916

[21] Appl. No.: 619,844

[22] Filed: Jun. 12, 1984

[51] Int. Cl.$^4$ ................. G01N 33/543; G01N 33/544; G01N 33/545; G01N 33/552

[52] U.S. Cl. ......................... 435/7; 436/501; 436/518; 436/527; 436/528; 436/531; 436/533; 436/534; 436/815; 436/829

[58] Field of Search ...................... 435/7, 810, 4, 176, 435/177; 436/527, 528, 529, 518, 534, 531, 532, 533, 829, 808, 809, 501

[56] References Cited

U.S. PATENT DOCUMENTS

| | | |
|---|---|---|
| 4,193,983 | 3/1980 | Ullman et al. |
| 4,235,792 | 11/1980 | Hsia et al. |
| 4,342,739 | 8/1982 | Kakimi et al. |
| 4,342,826 | 8/1982 | Cole |
| 4,372,745 | 2/1983 | Mandle et al. |
| 4,480,041 | 10/1984 | Myles et al. |
| 4,483,921 | 11/1984 | Cole |
| 4,517,303 | 5/1985 | Freytag et al. |

FOREIGN PATENT DOCUMENTS 8001515  7/1980  PCT Int'l Appl.

OTHER PUBLICATIONS

Petrossian et al., Biochimica et Biophysica Acta., 776, 217–227, (1984).
Haxby et al., *PNAS*, 61, 300, (1968).
Alving et al., *Biochem.*, 8, 1582, (1969).
Kinsky et al., *Biochem.*, 8, 4149, (1969).
Alving et al., *Liposomes*, pp. 209–287, (Marcel Dekker, 1983).
Freytag et al., *Biophys. J.*, 45, 360(6), (1984).
Janoff et al., *Clin. Chem.*, 29, 1587, (1983).
Szoka et al., *Ann. Rev. Biophys. Bioeng.*, 9, 467, (1980).
Deamer et al., *Liposomes*, pp. 27–51, (Marcell Dekker, 1983).
Reiss-Husson, *J. Mol. Biol.*, 25, 363, (1967).
Rand et al., *Chem. Phys. Lipids*, 6, 333, (1971).
Enoch et al., *PNAS*, 76, 145, (1979).
Eisen et al., *Meth. Immunol. Immunochem.*, 1, 351, (1967).
Warr, *Antibody as a Tool* . . . pp. 59–96, (Wiley, 1982).

Primary Examiner—Esther M. Kepplinger
Assistant Examiner—David A. Saunders
Attorney, Agent, or Firm—Ernest V. Linek; George W. Neuner

[57] ABSTRACT

This invention is directed to a new membrane lytic immunoassay. In one embodiment of this assay, an antigen is first covalently coupled with lipids and this antigen-lipid complex is mixed with a hexagonal phase forming lipid to form bilayer liposome vesicles additionally containing a self-quenching fluorescent dye. When this antigen-containing liposome is brought into contact with a solid surface coated with antibody molecules, binding occurs between the antigen and the antibody, disrupting the liposome and releasing the dye. To assay a biological fluid for free antigen the fluid is first contacted with the solid surface-antibody complex, to saturate the bound antibody. Binding by the liposomes is thereby inhibited, leading to reduced dye release. Comparing dye release against a standardized curve of dye release versus known antigen concentrations allows for rapid determination of the unknown antigen concentration in the biological fluid. Similarly, antibodies and other entities, e.g., enzymes, drugs, etc., may be determined using slightly modified versions of this assay.

39 Claims, 8 Drawing Figures

IMMUNOLIPOSOME ASSAY-METHODS AND PRODUCTS

STATEMENT OF GOVERNMENT SUPPORT

This invention was made with support of the Government of the United States of America by virtue of Grant Numbers CA 24553 and CA 00718, awarded by the National Institutes of Health. The Government has certain rights in this invention.

FIELD OF THE INVENTION

This invention is directed to a homogeneous solid-state immunoliposome assay and to products useful therein, especially in kit form. The assay utilizes the lateral phase separation of an antigenic liposome resulting in the destabilization and lysis of the liposome which may be quantified and employed in determining the presence and/or concentration of antigens, antibodies and like agents in biological fluids.

BACKGROUND OF THE INVENTION

High volume screening assays are commonly employed for detecting the presence of, and quantitatively measuring antigenic materials, antibodies and analytes in biological samples. For example, radioimmunoassay (RIA) techniques are commonly employed for clinical diagnostics. However, RIA procedures are often incompatible with large scale screening programs. Radiotracers, by their very nature, are of limited stability and they require special handling during use, special disposal techniques and sophisticated instrumentation.

Other immunoassay methods currently available include fluorescent and enzymatic techiques. Generally, these assays require a separation step, either by filtration or centrifugation in order to be interpreted. These separation requirements make the assay methods slow and difficult to automate.

Liposomes have previously been reported as useful components for immunoassays. For example, McConnell et al., U.S. Pat. No. 3,887,698, describe the use of liposomes containing stable free radicals in an electron paramagnetic resonance (EPR) monitored immunoassay. Mandle et al., U.S. Pat. No. 4,372,745, describe the use of liposomes as fluorescer containing microcapsules, useful in an immunoassay. This assay requires the use of a detergent such as, Triton X-100 to break the liposomes and release the fluorescent compound. Liposomes have also been employed as a marker carrier in an immunoassay described by Ullman et al., U.S. Pat. No. 4,193,983. Markers used in this assay included fluorescers, enzymes and chemiluminescent compounds.

Kinsky and his colleagues were the first to show that liposomes containing haptenated lipids could bind with an antibody and fix the complement thereof (Haxby et al., *Proc. Natl. Acad. Sci. USA*, 61 300 (1968); Alving et al., *Biochem.*, 8 1582 (1969); Kinsky et al., *Biochem.*, 8 4149 (1969)). The result was the lysis of the liposomes by the activated complement components.

Cole, U.S. Pat. No. 4,342,826, describes an immunoassay method which utilizes antigen-tagged, enzyme-encapsulated liposomes which are immunospecifically ruptured in the presence of the cognate antibody and an active complement. The assay utilizes the homogeneous phase reaction between the antibody and complement to release the enzyme marker. This complement mediated event has been the focal point for a large amount of literature (for a recent review, see Alving & Richards, *Liposomes*, Ostro, ed., 209-287 (Marcel Dekker, New York, 1983)).

Recently several noncomplement mediated liposome lytic assays have been developed. For example, binding of the antibody to haptens conjugated to a membrane lytic protein, melittin, blocks and liposome lytic activity of the melittin (Freytag et al., *Biophys. J.*, 45 360(a) (1984)). Binding of the antibody in the Lupus serum to liposomes containing cardiolipin prevents the lysis of the liposome by $Mg^{+2}$ ions (Janoff et al., *Clin. Chem.*, 29 1587 (1983)). While no complement is required each of these assays requires either a membrane lytic molecule or ion.

Although the previously described assays may be quite sensitive, they often involve many steps, and are sometimes difficult to reproduce and/or automate. Thus, new and more efficient assays are desirable.

SUMMARY OF THE INVENTION

The present invention is directed to an immunoassay wherein the lysis of the liposomes is a direct consequence of the immune complex formation. The assay of this invention is as sensitive as RIA, providing rapid determinations, yet it does not require the presence of membrane lytic molecules, ions, or active complements.

This invention is directed to a new membrane lytic immunoassay. Accordingly, said membrane lytic immunoassay comprises the steps of:

(a) forming liposomes containing the analyte of interest and a marker compound;

(b) providing a solid phase inert support having attached thereto a receptor for the analyte of interest;

(c) mixing said test fluid with said receptor-solid phase support of step (b) for sufficient time to saturate said receptor with any analyte present in said test fluid;

(d) mixing said liposomes formed in step (a) with said saturated receptor-solid phase support from step (c);

(e) determining the presence of marker compound released by the liposomes in step (d).

In one embodiment of this assay, an antigen is first covalently coupled to a lipid and this antigen-lipid complex is used in conjunction with an otherwise non-bilayer forming lipid or mixture of lipids to form stable bilayer liposome vesicles which additionally contain a self-quenching fluorescent dye. When this antigen and dye containing liposome is brought into contact with an inert solid surface having attached thereto, antibody molecules, rapid binding occurs between the antigen-lipid complex and the antibody, disrupting the liposome and releasing the dye. Release of the dye can be quantified using standard fluorometric measurements. To assay the amount of antigen in a test sample, the sample, original or diluted, is first added to the inert solid surface to saturate the attached antibody. Thus, the subsequent liposome binding and dye release are reduced. The amount of antigen in an unknown sample is then determined by comparison with the amount in known standards. The invention is also directed to products useful in said assay, especially in kit form.

DETAILED DESCRIPTION

Figure 1:
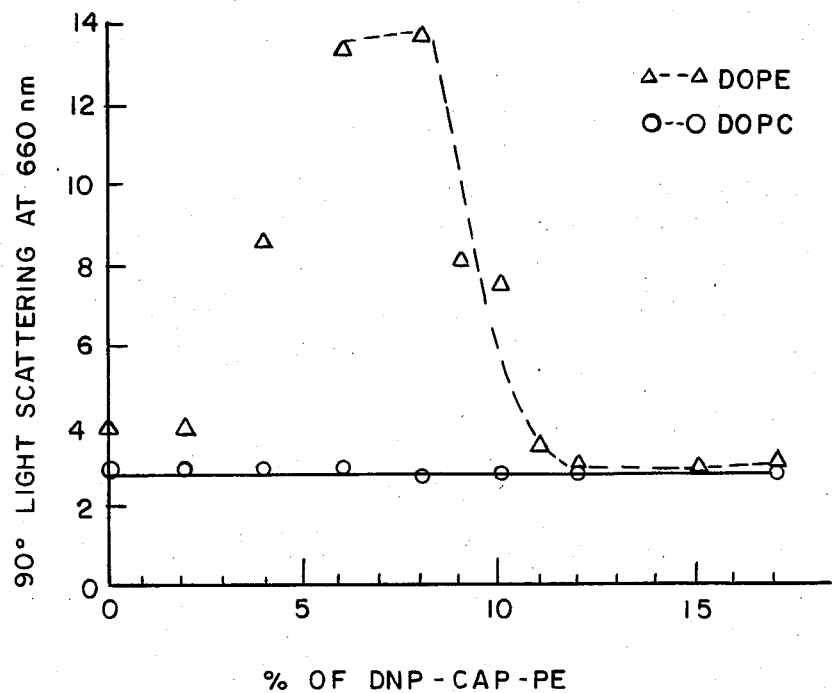
FIG. 1 illustrates the stabilization of DOPE and DOPC liposomes with DNP-cap-PE. 90° light scattering of the sonicated lipid were measured for DOPE (a) and DOPC (b) liposomes.

Liposomes are microscopic vesicles composed of closed lipid bilayers. See: Papahadjopoulos, *Ann. N.Y. Acad. Sci.*, 308 1 (1978). Due to their relatively simple composition and their flexibility for chemical, physical and immunological manipulations, liposomes are a favorite material for membrane lytic assays.

When compared to other immunoassay techniques, there are several advantages in using a membrane lytic immunoassay: (1) a single lytic event can lead to the release of many signal molecules and hence there is a high degree of signal amplification, (2) it is rarely necessary to separate the immune complex from the free antibody or antigen and hence it is generally a homogeneous assay; and (3) optical measurements such as colorimetric and fluorometric techniques can be used and hence it avoids any requirement for the use of radioisotopes. For these reasons, membrane lytic assays have received increasing attention in the recent development of immunoassays.

The immunoliposome assay of the present invention will be illustrated by refering to the assay for one particular entity, e.g. an antigen. The general principles and techniques described herein for assaying an antigen can then be applied to assay for other species such as, for instance antibodies, haptens, etc.

In order to aid in the understanding of the present invention, the following terms as used herein and in the claims have the following meanings:

Analyte—the compound or composition to be measured, which may be a ligand, such as an antigen, hapten or an antibody. For example, in a preferred embodiment, the analyte may be either an antigen or an antibody.

Ligand—any compound for which an immunological receptor naturally exists or can be made. When the ligand is an antibody, the immunological receptor can be an antigen or an anti-antibody.

Ligand-lipid complex—a covalently bonded specie comprising the analyte of interest and a lipid composition compatable with the lipid or lipids used to form the liposomes for the assay herein. If the ligand of interest cannot be directly used to stabilize the lipid bilayer for the formation of vesicles, the ligand must first be coupled to a suitable lipid using conventional coupling chemistry. Similar coupling chemistry is described herein below for coupling between the anti-ligand and the inert solid support. Lipids useful for such couplings include ($>C_{10}$) fatty acids, phospholipids, ($>C_{10}$) hydrocarbons, large cyclic hydrocarbons, polycyclic hydrocarbons and others readily selectable by those skilled in the art. The ligand-lipid complex is employed to stabilize an otherwise unstable liposome composition. For example, in one embodiment, an antigen covalently bound to a derivative of phosphatidylethanolamine (N-caproyl-) was employed to stabilize liposomes formed predominantly (88 mole percent) of phosphatidylethanolamine.

Marker compound—any compound capable of ready detection other than a radiotracer. Especially useful herein are markers such as enzymes, see Cole U.S. Pat. No. 4,342,825 (incorporated herein by reference) chemiluminescent species, colorogenic agents and fluorogenic agents. The most preferred marker compounds are self-quenching fluorescent dyes. These compounds include water soluble derivatives of fluorescein such as carboxyfluorescein and calcein. Another suitable marker is a combination of water soluble fluorophore, e.g., 8-amino-naphthalene-1,3,6-trisulfonic acid and a water soluble quencher, such as p-xylene bis(pyridinium)bromide. As the dye/quencher combination is released from the liposome at lysis, dilution allows for dequenching of and thus detection of the fluorophore. See for example, Ellens et al., *Biochem.*, 23 1532 (1984).

Receptor—any compound or composition capable of recognizing a particular spatial and polar organization of another molecule. Natural receptors include antibodies, enzymes, lectins, and the like. For any specific ligand, the receptor may be generally termed an antiligand. Depending upon the circumstances the terms may be interchangeable, i.e., receptors in one case can be ligands in another. For example, in a preferred embodiment, the receptor for an antigen is an antibody, while the receptor for an antibody is either an anti-antibody or, preferably, that antibody's cognate antigen.

System—a combination of analyte, ligand and/or receptor reagents, usually formulated with ancillary reagents such as buffers, salts, stabilizers and the like, and supplied in individual containers, generally in the form of an assay kit. For example, a system for detecting the presence and/or the concentration of an antigen would include appropriate containers with (1) antigen or a chemical derivative thereof in the membrane of liposomes and (2) a fluorescer or other suitable marker encapsulated in the liposomes of (1); (3) an antibody for the antigen attached to a solid support; and (4) antigen standards of known concentration for preparing a curve for comparison of known dye release with the unknown dye release or a predetermined comparison curve and one standard for a control. Alternatively, the kit can include merely: (1) suitable reagents for preparing the ligand-lipid complex; (2) other liposome forming components, as necessary; (3) a marker compound; (4) analyte standards; and (5) receptor standards. The user can readily formulate specific reagents depending upon the particular assay requirements at hand. A detection means can also be supplied as part of the system, but this is not typically required.

In one embodiment of this invention, an assay for an antigen involves the lateral phase separation of a liposome formed from an antigen-lipid complex resulting in the destabilization of the liposome and release of a marker compound such as a fluorescent dye.

Any lipid that is capable of forming the hexagonal ($H_{II}$) phase can be used in the practice of this invention. One such suitable lipid is an unsaturated phosphatidylethanolamine (PE) such as egg PE or dioleyl PE. Unsaturated PE by itself does not form stable liposomes at room temperature and neutral pH. Lipids in addition to PE which can form the $H_{II}$ phase include cardiolipin and phosphatidic acid. These lipids form the $H_{II}$ phase in the presence of a divalent cation, such as $Ca^{2+}$. No other natural lipids have been reported to form the $H_{II}$ phase under physiological conditions of temperature and salt concentration. However, the general requirement for the structure of an $H_{II}$-forming lipid is a relatively small hydrophilic group coupled to a relatively bulky hydrophobic moiety (the overall molecular shape being cone-like). Therefore, synthetic lipids may readily be prepared, which, under an appropriate molecular configuration (cone-like) will also exhibit the $H_{II}$ phase, and be useful in the practice of this invention.

Furthermore, it has been postulated that lipid molecules having a complementary shape, that is, an inverted cone, can form stable bilayer liposomes, together with the above-described $H_{II}$ forming lipids. These lipid molecules would comprise a bulky hydrophilic group coupled to a small hydrophobic moiety. It will be apparent to those skilled in the art that the conjugated complex of a water-soluble ligand, such as an antigen, and a lipid having sufficient hydrophobic character, will have the molecular configuration of an inverted cone. Thus, this type of ligand-lipid complex will be useful to stabilize an otherwise unstable liposome bilayer comprised of the $H_{II}$ forming lipid. See Cullis and DeKruijff, *Biochem. Biophys. Acta*, 559 339 (1979), the disclosure of which is incorporated herein by reference.

Using an $H_{II}$ forming lipid and a ligand-lipid complex, such as an antigen-lipid complex, stable liposomes can be prepared by sonication, dialysis, or by other conventional techniques, and a marker compound such as a self-quenching fluorescent dye can be entrapped with the liposomes. When the antigen-containing liposomes come into contact with an inert solid surface having attached thereto the appropriate antibody molecules that recognize or react with the antigen, the antigen-lipid complexes laterally migrate and bind with the antibodies. This lateral phase separation of the liposomes results in a rapid bilayer to hexagonal phase transition, leading to the release of the entrapped marker. Thus, for example, a fluorescent signal is released which can be readily measured without the need for separation of any reagents or other material from the inert solid surface.

To assay for free antigen in a biological fluid such as serum, the serum is first added to the antibody attached to the inert solid surface thereby binding the antigen to the attached antibody. Thus, the binding ability of the liposome is inhibited, leading to a reduced level of dye release. To assay for free antibody, the serum is first added to the liposomes. Since the free antibody is not multivalent, no phase separation of the liposome occurs. Instead, the binding sites of the antigen-lipid complex are filled with free antibody, again reducing the binding ability of the liposome to the immobilized antibody.

The assay of this invention is carried out in an aqueous medium at a moderate pH, such as neutral pH, generally close to optimum assay sensitivity, without the need for separation of the assay components or products. The assay zone for the determination of analyte is prepared by employing an appropriate aqueous solution, normally buffered containing the unknown sample, which may have been subject to prior treatment, the liposome-analyte-fluorescer reagent, any auxiliary materials associated with production of the detectible signal, as well as when appropriate, a modified or unmodified receptor bound to a solid, inert support.

The concentration of a ligand or anti-ligand as the analyte in the biological sample will affect the degree of binding between the solid support bound receptor and the immunoliposome complex and influence the production of the detectible signal.

In carrying out the assay an aqueous medium will normally be employed. Other polar solvents may also be employed, usually oxygenated organic solvents of from 1 to 6, more usually from 1 to 4 carbon atoms, including alcohols, ethers and the like. Usually these cosolvents will be present in less than about 40 volume percent, more usually in less than about 20 volume percent.

The pH for the medium will usually be in the range of about 4 to 10, more usually in the range of about 5 to 9, and preferably in the range of about 5.5 to 8.5. The pH is chosen so as to maintain a significant level of specific binding by the receptor while optimizing signal producing proficiency. In some instances, a compromise will be made between these two considerations. Various buffers may be used to achieve the desired pH and to maintain the pH during the determination. Illustrative buffers include borate, phosphate, carbonate, Tris, Tris HCl, barbital and the like. The particular buffer employed is not critical to this invention but in individual assays, one buffer may be preferred over another.

Moderate temperatures are normally employed for carrying out the assay and usually a constant temperature is maintained during the period of the assay. The temperatures for the determination will generally range from about 10° to 50° C., preferably from about 15° to 40° C., and more preferably be about 22° C., where applicable.

The concentration of analyte which may be assayed will generally vary from about $10^{-4}$ to $10^{-15}$ molar, more usually from about $10^{-6}$ to $10^{-13}$ molar. Concentrations such as whether the assay is qualitative, semi-quantitative or quantitative, the particular detection technique and the expected concentration of the analyte of interest will normally determine the concentrations of the other reagents.

Although the concentrations of the various reagents will generally be determined by the expected concentration range of interest of the analyte, the final concentration of each of the reagents will normally be determined empirically to optimize the sensitivity of the assay over the range of interest.

Attachment of the receptor to the inert solid surface may be accomplished using any technique available to the skilled artisan. Such techniques include, but are not limited to, adsorption, absorption, ionic bonds, covalent bonds, hydrogen bonds, and the like. Typically, glass and water insoluble polymers are used as the support for the receptor. The support may be in any shape or form. For example, flat objects such as glass slides, polymeric disks or strips, the walls of a test tube, or widely available beads can be employed as the support herein. The bonds between the receptor and the support should be strong enough so that normal washing procedures, or contact with aqueous solutions, including a test serum, do not destroy the attachment means.

One suitable form of chemical binding is to provide bridges of covalent character between the solid support and the receptor. For this purpose the solid support is selected so that it contains or can be provided with suitable reactive functional groups, for example, amino groups, hydroxyl groups, and carboxyl groups, to enable the receptor to be easily bound to the solid support. Especially useful are bridges between the solid support and the receptor having chemical bonds of a covalent nature.

Functional groups generally useful as bridge groups between the inert support and the receptor are generally selected from:

receptor-NH-CS-NH-support
receptor-NH-CO-NH support
receptor-N=N-support
receptor-O-CO-support
receptor-NH-CO-support
receptor-CO-NH-support
receptor-NH-C(=O)-O-support
receptor-NH-C-(=NH)-NH-support The particular bridge between the receptor and the support is not a critical part of the assay of this invention. The bridge may be of any type, or a mixture of types, as its only purpose is to prevent the receptor from being washed away from the support. The bridge is usually hydrophilic and inert to the ligand-receptor binding.

Polymers having a three-dimensional network are useful as inert solid supports herein. Such polymers, which may be swellable in water or aqueous solutions, are completely insoluble and are generally considered inert. Examples of suitable polymers include the copolymerizates obtained by cross-linking substances containing a plurality of hydroxyl groups such as the carbohydrates and sugar alcohols, for example, dextran, starch, dextrins and other polysaccharides, and polyvinyl alcohols, with a bifunctional substance, for example, substances of the type X-R-Z, wherein, for example, X and Z are halogen or epoxy groups and R is the residue of the bifunctional substance, usually an aliphatic carbon chain of from 3 to 10 carbon atoms.

The receptor is bound to the inert polymer under mild conditions, in order not to appreciably reduce its immunochemical reactivity.

Especially useful supports in this assay are glass (slides, beads, etc.), latex, and the water swelling gels such as Sephadex and polyacrylamide. The support is preferably used in such a form that a large contact area is obtained, and the particle or bead form is most suitable.

The assay of the present invention is most preferably a homogeneous assay. Thus, the size and/or the density of the solid support should be chosen so as to give minimal background interference, e.g., light scattering, to the marker compound. If interference is encountered, large particles, and/or high density particles should be employed such that the particles will settle to the bottom of the assay tube in a few minutes, thus eliminating any interference with the detectability of the marker compound. This delay can be readily included within an automated assay system by incorporating a momentary (1-2 min.) delay between mixing of reagents and the assay reading.

The assay of the present invention may be illustrated by reference to the preparation of immunoliposomes for one embodiment as described below. Immunoliposomes for other embodiments can be prepared in an analogous fashion.

There are many methods for the preparation of liposomes. Some of them are used to prepare small vesicles (d<0.05 micrometer), some for large vesicles (d>0.05 micrometer). Some are used to prepare multilamellar vesicles, some for unilamellar ones. For the present invention, unilamellar vesicles are preferred because a lytic event on the membrane means the lysis of the entire vesicle. However, multilamellar vesicles could also be used, perhaps with reduced efficiency. Methods for liposome preparation are exhaustively described in several review articles such as Szoka and Papahadjopoulos, *Ann. Rev. Biophys. Bioeng.*, 9 467 (1980), Deamer and Uster, in *Liposomes*, ed. M. J. Ostro, Marcel Dekker, New York, 1983, p. 27-51. The recently published monographs *Liposome Technology*, ed. G. Gregoriadis, CRC Press, Boca Raton, also contain up-to-date information, especially in volume I.

Dioleyl phosphatidylethanolamine (DOPE) does not form stable bilayer liposomes at room temperature and neutral pH. However, stable unilamellar liposomes were prepared by mixing DOPE with a minimum of 12% of a haptenated lipid, N-(dinitrophenylamino caproyl)-phosphatidylethanolamine (DNP-cap-PE). When these liposomes containing a self-quenching fluorescent dye such as calcein, come into contact with rabbit anti-DNP IgG which has been adsorbed on a glass surface, lysis of the liposomes occurs with the release into the medium of the self-quenching fluorescent dye. Normal rabbit IgG has little effect. Free rabbit anti-DNP IgG only induces the aggregation of the liposomes but does not cause any dye release. Liposomes composed of dioleyl phosphatidylcholine and DNP-cap-PE do not lyse when added to the glass surface coated with either rabbit anti-DNP IgG or normal rabbit IgG because phosphatidylcholine does not form the $H_{II}$ phase.

As described above, the design of the assay was based on the inability of unsaturated PE to form stable bilayer liposomes at physiological conditions (Reiss-Husson, *J. Mol. Biol.*, 25 363 (1967); Rand et al., *Chem. Phys. Lipids*, 6 333 (1971); Callis et al., *Biochem. Biophys. Acta*, 559 399 (1979)). The minimal amount of DNP-cap-PE required to stabilize the DOPE bilayer liposomes was determined so that a small perturbation would lead to a decrease in the effective concentration of the ligand-lipid complex in the bilayer, resulting in a destabilization of the bilayer. The perturbation factor was designed to be the binding of the ligand-lipid complex with the immobilized, multivalent anti-ligand. This minimal amount will vary with temperature, pH and the particular ligands or anti-ligands used in the assay. However, the appropriate amount can readily be determined by those skilled in the art using routine experimentation based upon the principles described both herein and elsewhere in the available literature.

Figure 8:
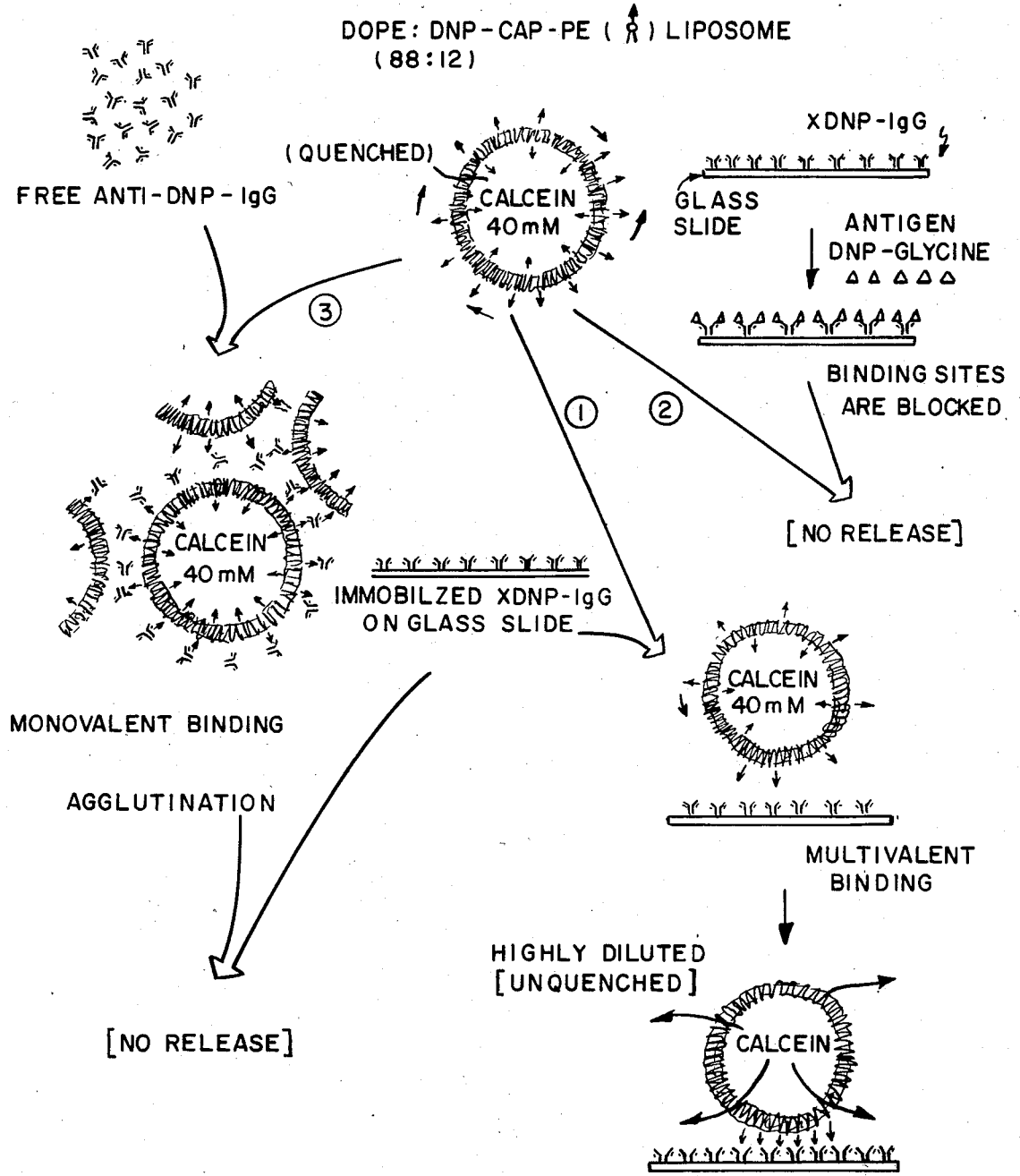
FIG. 8 is a schematic representation of the solid-state immunoliposome assay of the present invention.

While not wishing to be bound to any particular theory, one explanation for the principles of the assay of the present invention involves the lateral phase separation of the phospholipids. As shown in FIG. 8, ligand-lipid complex rapidly diffuses in the plane of the fluid lipid bilayer with a diffusion coefficient about $1 \times 10^{-8}$ cm$^2$/sec (see review, Peters, *Cell Biol. Intern. Rpts.*, 5 733 (1981)). This means that it will only take about a fraction of a second for ligand-lipid complex to diffuse to the area of contact between the liposomes and the anti-ligand bound to the glass surface. The formation of immune-complexes prevents the random diffusion of the ligand-lipid complex away from the surface after contact. Thus, the ligand-lipid complex is rapidly trapped in the contact area. Such lateral phase separation effectively decreases the ligand-lipid complex concentration in the liposome bulk bilayer and leads to the destabilization of liposomes. It is estimated that the entire process takes only a few seconds or less at room temperature. While this mechanism remains speculative, it is consistant with the observation that the free bivalent antibody does not induce liposome leakage. Binding of the bivalent antibody to the ligand-lipid complex cannot bring about extensive phase separation. In fact, aggregation of the liposomes crosslinked by the bivalent antibody was observed.

The assay and products of the present invention will be further illustrated with reference to the following examples, which aid in understanding the invention, but are not to be construed as a limitation on the scope of the invention, which is set forth in the appended claims. All percentages reported herein are, unless otherwise specified, mole percent. All temperatures are expressed in degrees Celsius and are uncorrected.

EXAMPLE 1

Stabilization of DOPE Liposome Bilayer by DNP-cap-PE

Formation of a stable liposome was monitored by 90° light scattering at 660 nm. To determine the minimum amount of DNP-cap-PE which would stabilize the DOPE bilayer, various amounts of DNP-cap-PE were mixed with DOPE or DOPC and the lipid mixtures were sonicated for 20 minutes before the measurement of light scattering. When stable sonicated liposomes were formed, the turbidity of the suspension was low and hence low light scattering was detected. As shown in FIG. 1, at concentrations above 12% DNP-cap-PE, stable DOPE liposomes were generated. Between 6 to 11%, liposome suspensions were quite turbid and hence exhibited a high level of light scattering. Below 6%, large aggregates of lipid were seen and the light scattering was again low. Pure DOPE (without the ligand-lipid complex) only forms large aggregates even after prolonged sonication. In contrast, DOPC formed stable, low light scattering liposomes at all concentrations of DNP-cap-PE. It was concluded that a minimum of 12% DNP-cap-PE was required for stable DOPE liposome formation. This composition was used for all subsequent experiments.

EXAMPLE 2

Size of Liposomes

Figure 2:
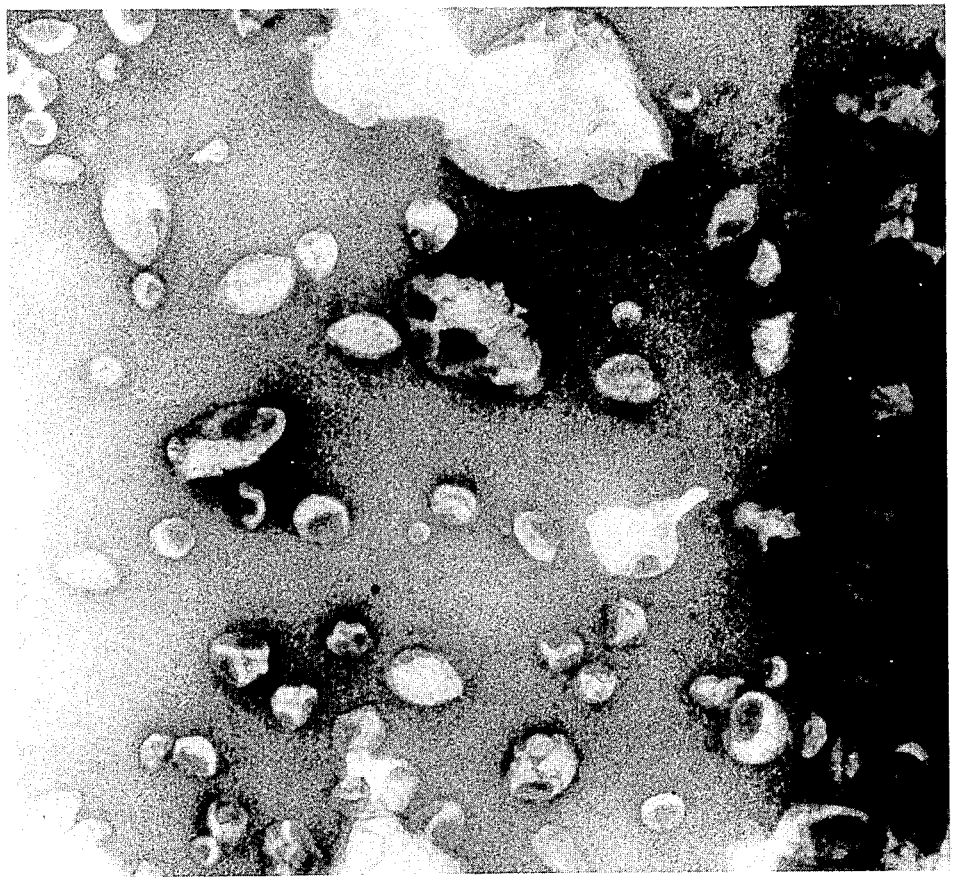
FIG. 2 is a negative stain electron microscopic photograph of DOPE-DNP-cap-PE (88:12) liposomes at a magnification of $1.12 \times 10^6$.

Sonicated liposomes composed of DOPE:DNP-cap-PE (88:12) (hereafter called DOPE liposomes) were unilamellar and relatively homogeneous in size as examined by negative stain electron microscopy (FIG. 2). The average diameter of the liposomes was 908±134 angstroms.

EXAMPLE 3

Trapped Volume of Liposomes

From the average diameter of the DOPE liposomes, the trapped or encased volume of the liposome can be calculated according to Enoch et al., *Proc. Natl. Acad. Sci. USA*, 76 145 (1979) to be 2.66 microliter/micromole lipid. The trapped volume was also directly estimated by measuring the amount of calcein trapped in the liposomes after the removal of the untrapped calcein by gel filtration. This was done by constructing a standard curve of fluorescence intensity vs. calcein concentration (0 to 0.5 micromolar); and by measuring the $^3$H-cpm in a liposome suspension additionally containing a trace amount of hexadecyl [$^3$H] cholestanyl ether to determine the lipid mass. Assuming the calcein concentration inside the liposomes was 40 millimolar, the trapped volume was determined to be 2.08 microliter/micromole lipid. This is in agreement with the value calculated from the size of the liposomes. The trapped volume of the DOPC:DNP-cap-PE (88:12) liposomes (hereafter called DOPC liposomes) was 0.54 microliter/micromole, indicating that these liposomes were much smaller in size. DOPE or DOPC liposomes containing calcein could be stably stored at 4° C. for at least one week without significant dye leakage.

EXAMPLE 4

Dye Release upon Liposome-Antibody Interaction

Figure 3:
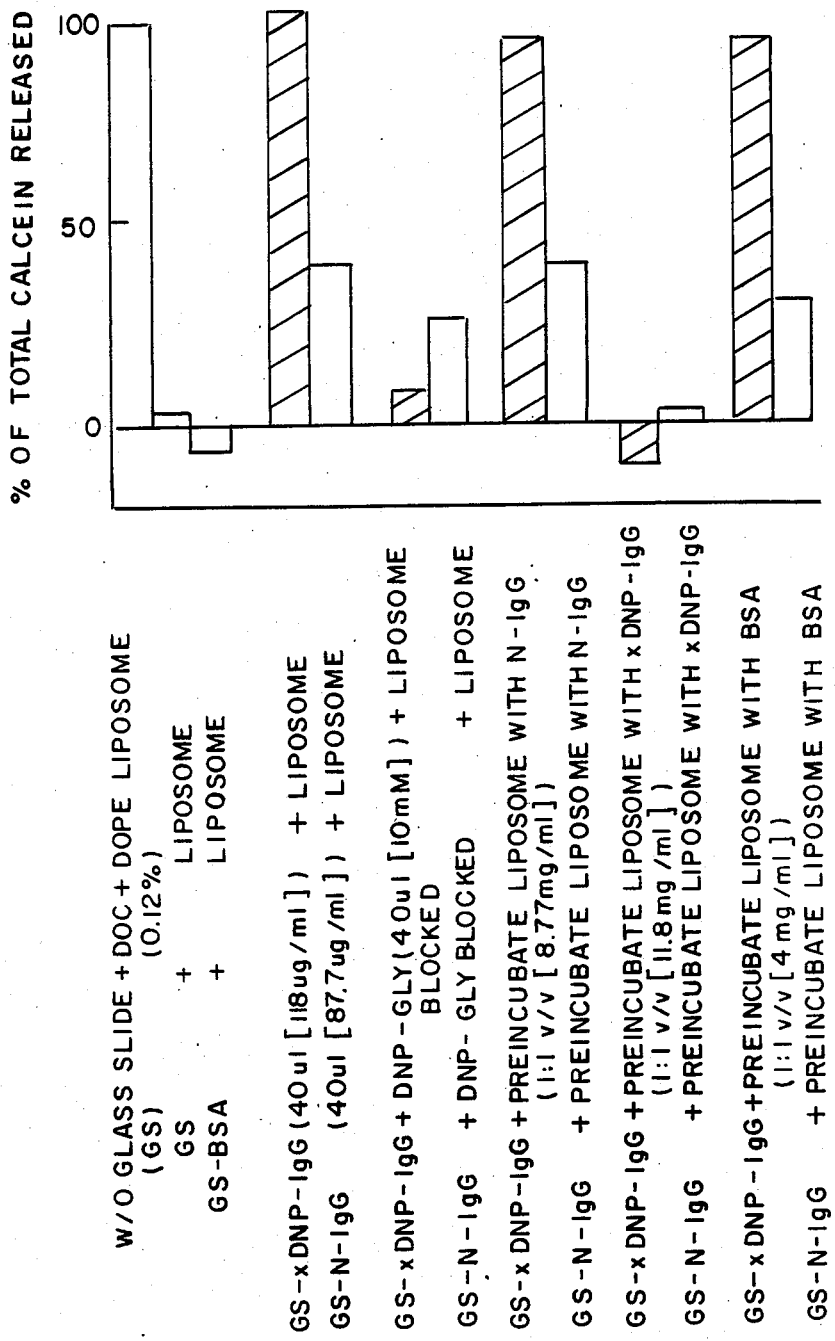
FIG. 3 illustrates the immunospecificity of DOPE liposome lysis by antibody attached to the glass slide.
Figure 4:
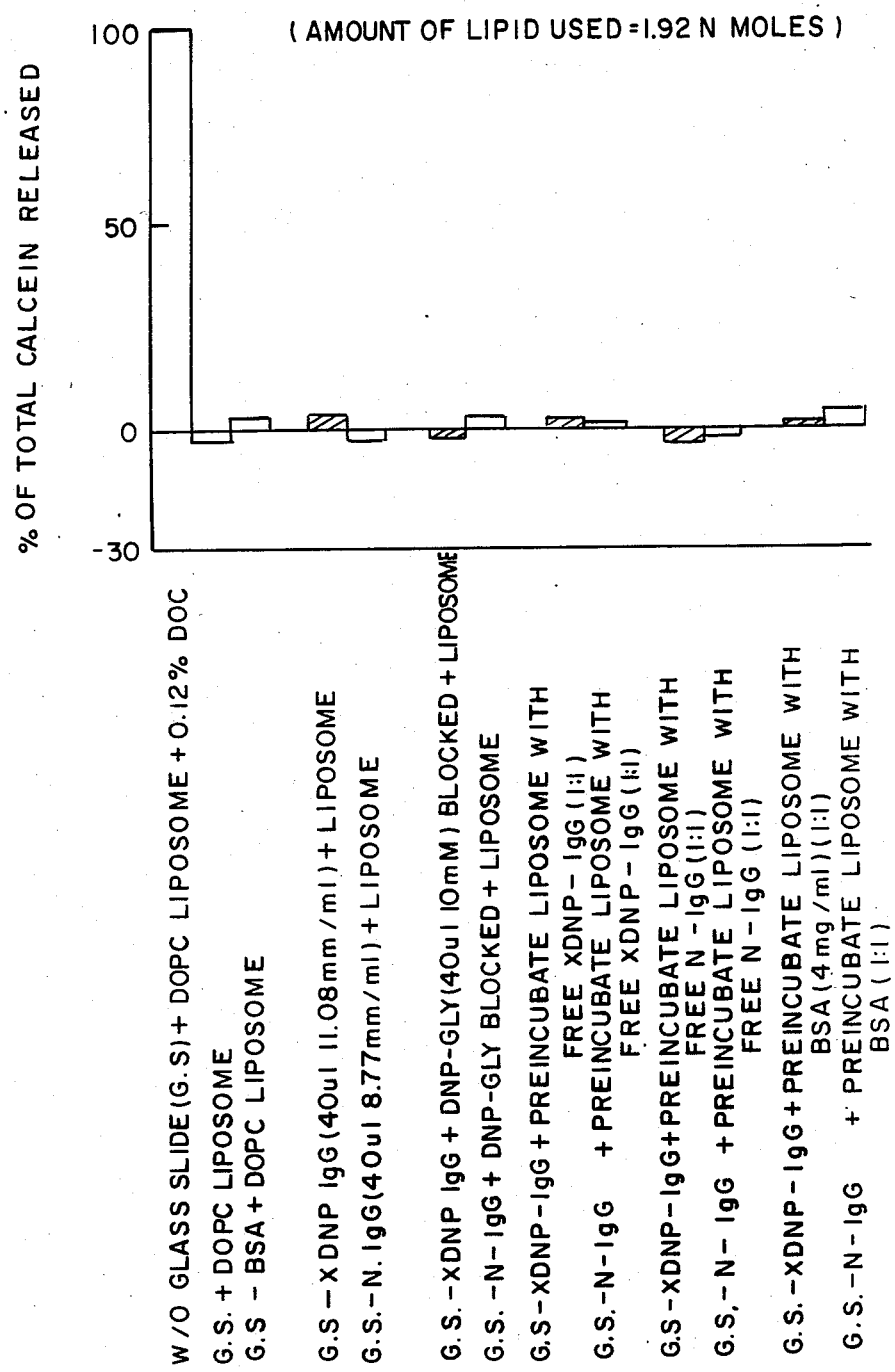
FIG. 4 illustrates the immunospecificity of DOPC liposome lysis by antibody attached to a glass slide.

In order to measure liposome lysis, calcein was trapped at a 40 micromolar concentration inside the liposome. At this concentration calcein fluorescence is self-quenched. Fluorescence is greatly enhanced when the dye leaks out of the liposomes (Allen et al., *Biochim. Biophys. Acta*, 597 418 (1980)). Using a glass surface coated with various types of protein, the ability to induce the calcein release from the liposomes was tested. As can be seen from FIG. 3, bare glass surface and glass surface coated with BSA could not induce liposome leakage. However, when DOPE liposomes came in contact with the glass surface coated with anti-DNP IgG, all of the entrapped calcein was released. Glass surface coated with normal IgG did have some effect but the magnitude was much less than that of the anti-DNP IgG. Dye release was blocked by a pretreatment of the glass surface with free hapten, DNP-Gly, or by a preincubation of the liposomes with free anti-DNP IgG, but not by free normal IgG or BSA. These results strongly indicate that the dye release from the DOPE liposomes is a direct result of the antibody-hapten binding at the glass surface. DOPC liposomes were very stable; none of the glass surface types tested could induce the dye release (FIG. 4).

EXAMPLE 5

Effect of Immobilized Antibody Concentration on Dye Release

Figure 5:
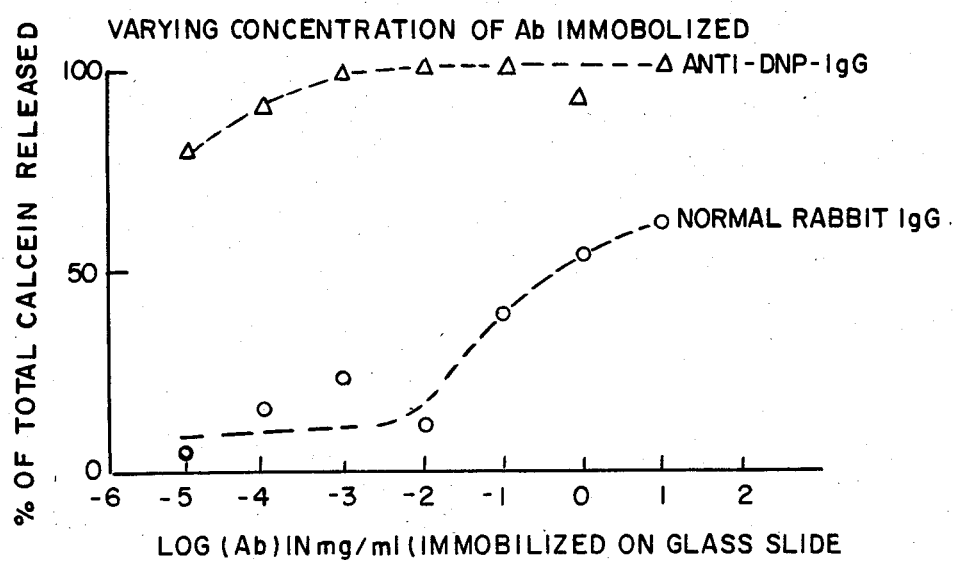
FIG. 5 illustrates the effect of the attached antibody concentration on DOPE liposome lysis. Anti-DNP IgG (c) or normal IgG (d) at indicated concentrations was used to coat a glass slide, and the DOPE liposome lysis was measured by calcein release.

The concentrations of the IgG solution used in the coating of the glass surface was also varied. FIG. 5 shows that the dye release was dependent on the antibody concentration on the glass surface. Nearly total release was observed for glass surface coated with anti-DNP IgG solution of a concentration greater than 1 microgram/ml. Below this concentration, progressively lower release was seen. At high concentrations (above 10 microgram/ml), normal IgG also showed a nonspecific effect on liposome lysis, however the magnitude was much lower than those caused by the anti-DNP IgG. For the subsequent experiment, Example 6, below, an IgG concentration of 10 microgram/ml to coat the glass surface was used.

EXAMPLE 6

Inhibition of Dye Release by Free Hapten

Figure 6:
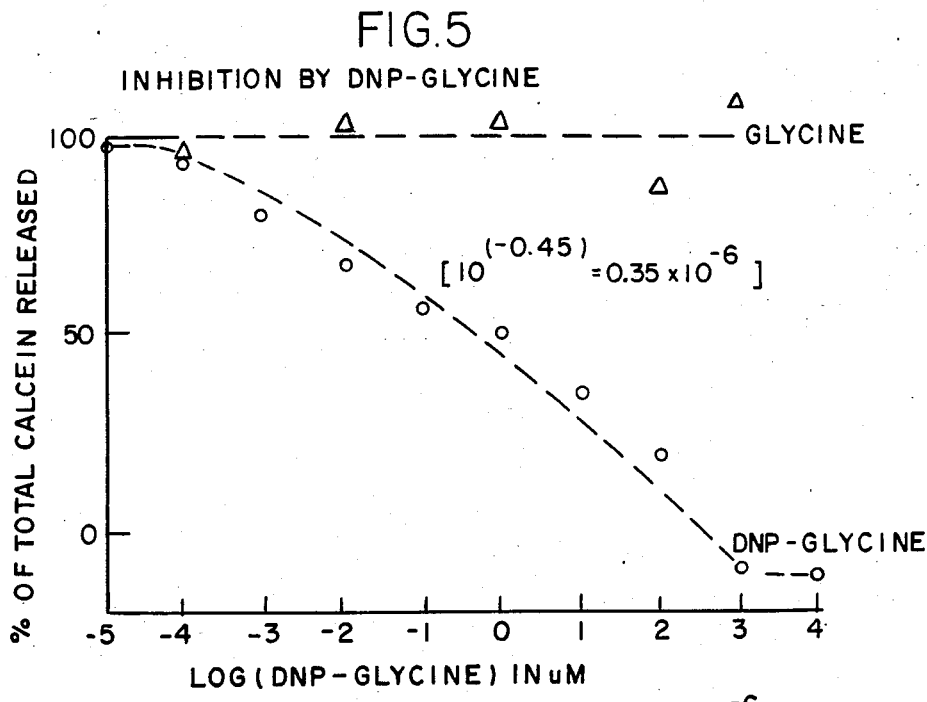
FIG. 6 illustrates the inhibition of DOPE liposome lysis by free hapten. DNP-Gly (e) or Gly (f) of indicated concentration was added to attached anti-DNP IgG on a glass slide before liposome addition.

The inhibitory effect of the free hapten to liposome lysis was also examined. As can be seen in FIG. 6, free hapten, DNP-Gly could effectively inhibit the dye release from the DOPE liposomes. The concentration of the free hapten which caused 50% inhibition was calculated to be 0.35 micromolar, which was equal to 14 picomole in 40 microliter of the preincubation medium. A non-hapten analog, Gly, had no effect on the dye release even at 1 millimolar concentration.

EXAMPLE 7

Inhibition of Dye Release by Free Antibody

Figure 7:
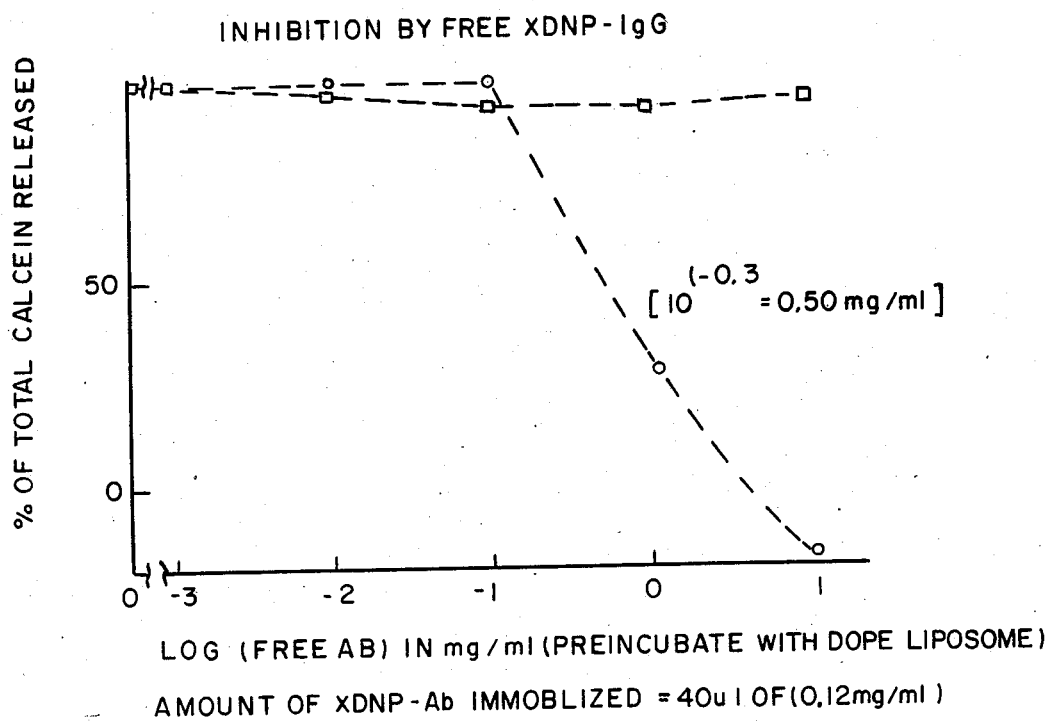
FIG. 7 illustrates the inhibition of DOPE liposome lysis by free antibody. Liposomes were preincubated with free anti-DNP IgG (g) or normal IgG (h) at indicated concentrations before adding to the attached antibody on a glass slide.

Free anti-DNP IgG did not cause dye release even at 10 mg/ml. However, visible aggregation of the liposomes of DOPE or DOPC type was observed when free anti-DNP IgG was preincubated with the liposomes. Preincubation of the DOPE liposomes with free anti-DNP IgG, but not the normal IgG, caused inhibition of the dye release (FIG. 7). Fifty percent inhibition took place at the free antibody concentration of 0.5 mg/ml, which is equal to 2.5 microgram in a 5 microliter preincubation volume.

Materials

Dioleyl phosphatidylethanolamine (DOPE), dioeyl phosphatidylcholine (DOPC) and N-(dinitrophenylaminocaproyl)-phosphatidylethanolamine (DNP-cap-PE) were purchased from Avanti Polar Lipids, Inc. (Birmingham, Ala.). Calcein, N-(dinitrophenyl)-glycine (DNP-Gly), and glycine were purchased from Sigma Chemical Co. (St. Louis, Mo.). Other reagents were analytical grade.

ANTIBODY

Anti-DNP serum was prepared from rabbits immunized with DNP-derivatized bovine serum albumin (BSA) (Eisen et al., *Meth. Immunol. Immunochem.*, 1 351 (1967)) and was a generous gift from Dr. Stephen Kennel. IgG fractions were purified from the serum by the protein-A affinity column chromatography (Warr, *Antibody as a Tool: The Applications of Immunochemistry*, Marchalonis and Warr, eds., 59–96 (John Wiley and Sons, New York, 1982)) and stored in phosphate buffered saline (PBS) at −20° C. Antibody was attached to glass surface by adding 40 microliters of IgG solution at various concentrations to a spot 1.5 cm in diameter on a clean glass slide. After 20 minutes at room temperature, the slide was washed thoroughly with from 6 to 8 ml PBS, blotted to dryness except the spot, and immediately used for the subsequent experiment.

LIPOSOME PREPARATION

In routine experiments, DOPE or DOPC (8.8 micromole) DNP-cap-PE (1.2 micromole) and trace amount of hexadecyl [$^3$H] cholestanyl ether (final specific activity $5.7 \times 10^9$ cpm/mol) were mixed and evaporated free of solvent with a stream of $N_2$ gas. The dry lipid was vacuum dessicated for at least 30 minutes. One hundred microliters of PBS containing 4 micromoles calcein, pH 7.4, was added. The mixture was sonicated for 20 minutes at room temperature in a bath sonicator (Laboratory Supplies, Inc., Hicksville, N.Y.) until a uniform translucent liposome suspension was obtained. The liposome suspension was then chromatographed on a Biogel A50m column to remove any untrapped calcein. The liposome eluted with PBS in the void volume fractions and was detected by counting $^3$H radioactivity, pooled and stored at 4° C.

LIPOSOME-ANTIBODY INTERACTIONS

Liposomes suspension (0.9 to 1.9 nanomole lipid in 5 to 45 microliters) was added to the spot on the glass slide which had previously been coated with IgG. After 20 minutes incubation in a moist chamber at room temperature, the glass slide was rinsed with 2 ml PBS to quantitatively transfer the liposomes into a quartz cuvette. The fluorescence was measured with a Perkin Elmer LS5 spectrofluorometer with lambda $_{ex}$=490 nm and lambda $_{em}$=520 nm. The total calcein fluorescence in the liposome was measured after the addition of sodium deoxycholate to a final concentration of 0.12%. The percent of dye release is defined as:

$$\% \text{ release} = \frac{F - F_o}{F_t - F_o}$$

where $F_o$ and $F$ are the calcein fluorescence of the liposome sample before and after the interaction with the immobilized antibody, respectively. $F_t$ is the total calcein fluorescence after releasing with the deoxycholate.

For the inhibition of dye release, free hapten in 40 microliters was added to the immobilized antibody on the glass slide and incubated for 20 minutes at room temperature before the addition of the liposomes. For the inhibition by free antibody, equal volumes of liposome and antibody were mixed and preincubated for 20 minutes at room temperature before being added to the glass slide.

90° C. LIGHT SCATTERING OF LIPOSOMES

In order to test for the liposome formation, sonicated lipids were diluted 100 fold in PBS. 90° light scattering was measured in a Perkin Elmer LS5 spectrofluorometer at lambda $_{ex}$=lambda $_{em}$=660 nm with a slit width of 3 nm.

ELECTRON MICROSCOPY

Liposome (0.75 micromole/ml) were negatively stained with 0.5% aqueous uranyl acetate and viewed in a Hitachi 600 electron microscope operated at 75 KV. The size of the liposomes was measured on photographically enlarged micrographs.

The method of the present invention can be applied to a wide variety of analytes. Antibodies, both polyclonal and monoclonal, can be raised using standard immunological techniques to numerous analytes. Other membrane-lytic techniques are also contemplated herein, for example, detection of enzymes or enzyme substrates using the assay of the present invention can be accomplished in a manner analogous to the detection of antigens or antibodies described supra.

In general, an enzyme substrate, which has been coupled to a suitable lipid (if necessary) is mixed with an $H_{II}$ forming lipid such as DOPE to form stable liposomes containing a marker, such as the fluorescent dye. Interaction between these liposomes and the appropriate enzyme bound to a solid support causes lysis of the liposomes, releasing the fluorescent dye. Calibration of dye release is accomplished using standard enzyme or substrate concentrations and inhibition of dye release by unknown quantities of enzyme or substrate in a biological test sample may readily be determined and the concentration calculated from the standard plots.

Enzymes detectable by the assay of the present invention include, but are not limited to; oxidoreductases such as alcohol dehydrogenase, glycerol dehydrogenase, glyoxylate reductase, L-lactate reductase, malate reductase, glucose 6-phosphate dehydrogenase, mannitol 1-phosphate dehydrogenase, L-lactate dehydrogenase, glucose oxidase, galactose oxidase, L-amino acid oxidase, D-amino acid oxidase, polyphenol oxidase, ascorbate oxidase, catalase, peroxidase; hydrolases such as carboxylic ester hydrolases, cholinesterase, phosphoric monoester hydrolase, alkaline phosphatase, phosphoric diester hydrolase, phospholipase C (when the lipid used to form the liposomes is not a phospholipid); glycoside hydrolases including alpha-amylase, cellulase, lysozyme, beta-galactosidase, amyloglucosidase, beta-glucuronidase; peptidyl-amino acid hydrolase, carboxypeptidase A, peptidyl-peptide hydrolase, alpha-chymotrypsin, papain, urease, inorganic pyrophosphataseg; lyases such as carbon-carbon lyases, e.g., aldehyde lyases, such as aldolase; carbon-oxygen lyases, e.g., hydrolases, such as carbonic anhydrase; carbon-nitrogen lyases, e.g., ammonia lyases, such as histidase.

The assay of the present invention can be employed in the detection and concentration calculation of circulating hormones in biological samples. Antibodies to these hormones may be raised using standard immunological techniques. Binding the antibodies to the inert solid support allows for lysis of liposomes comprised of an $H_{II}$ forming lipid and the hormone-lipid complex. A dye or enzyme can be encapsulated in the liposome as a marker compound. These hormones include thyroid hormones such as thyroxine, triiodothyronine, parathyroid hormone and calcitonin; pancreatic hormones such as insulin, proinsulin, and glucagon; pituitary hormones including prolactin, adrenocorticotropic hormone, tyrotropin, oxytocin, and vasopressin; uterine and placental hormones such as chorionic gonadotropin, placental lactogens, chorionic thyrotropin and relaxin; steroid hormones including estradiol, estrone, estriol, testosterone, and dihydrotestosterone; growth factors such as urogastrone, nerve growth factors and the somatomedins.

Similarly, the method may be usefully applied to the intracellular messengers, the cyclic nucleotides and prostaglandins.

The present invention may likewise be applied to the screening of circulating levels of therapeutic drugs, e.g. the cardiac glycosides; digoxin, digitoxin, anticonvulsants, diphenylhydantoin, mesantoin, phenobarbital, and mephobarbital. Of particular interest are those drugs with narrow therapeutic index, i.e., a certain minimal circulating level is required for therapeutic efficacy while a moderately higher level elicits toxic or harmful reactions.

The procedure may also be adapted to screening for antibodies raised against antibiotics, or to the antibiotics themselves, such as penicillins, cephalosporins, thienamycins, clavulanic acids, monobactams, streptomycin, and tetracyclines, chlortetracycline, oxytetracycline, and tetracycline, chloramphenicol, erythromycin, caromycin, polymyxin B. The aminoglycoside antibiotics gentamycin, amikacin, tobramycin, kanamycin and neomicin employed in the management of aerobic gram negative bacillary infections can be conveniently assayed by the present invention.

Likewise, this method may be applied to the detection and estimation of drugs of abuse such as opiates—morphine, heroin, meperidine and methadone; ergot alkaloids such as lysergic acid diethylamide; marijuana; barbiturates and cocaine and its derivatives.

The method is not restricted to small molecules. Macromolecular species including DNA, and large antigens such as egg albumin, can be directly or after conjugation with suitable lipids used to form stable bilayer liposome vesicles together with an $H_{II}$ forming lipid. Thus, the present invention can also be applied to detection of macromolecular species such as large antigens, plasma proteins, hepatitis associated antigens, histocompatibility markers, and the like.

Since the present invention is very simple in performance and does not employ unstable or hazardous reagents, the assay method is applicable in environments which are less well-equipped and less sophisticated than typical diagnostic laboratories. For example, the assay method can be applied to screening food and environmental toxins. In food screening, important antigens would be mycotoxins and natural toxicants. This area involves such major toxins as aflatoxins, ochratoxin, patulin, penicillic acid, zearelonone; and tricothecene toxins, as well as toxic metabolites such as ipomeamerone that occur naturally in foods. In addition to the natural toxicants there are a wide variety of environmental contaminants, the presence of which in foods, even in trace amounts, poses a significant threat to mankind. These may be industrial byproducts or pesticides, e.g., polychlorinated biphenyls, chlorinated dibenzo-p-dioxins, chlorinated dibenzofurans, heptachlorepoxide, dieldrin, and DDT, 1,1'-(2,2,2-Trichloroethylidene)-bis(4-chlorobenzene).

The present invention has been described in detail, including the preferred embodiments thereof. However, it will be appreciated that those skilled in the art, upon consideration of the present disclosure, may make modifications and improvements on this invention and still be within the scope and spirit of this invention as set forth in the following claims.

What is claimed is:

1. An immunoassay method for detecting or quantifying an analyte of interest in a test fluid, said method comprising:
    (a) forming liposomes having the analyte of interest incorporated onto the surface membrane thereof and a marker compound incorporated in the interior aqueous phase thereof;
    (b) providing a solid phase inert support having attached thereto a receptor for the analyte of interest;
    (c) mixing said test fluid with said receptor-solid phase support of step (b) for sufficient time to saturate said receptor with any analyte present in said test fluid;
    (d) mixing said liposomes formed in step (a) with said saturated receptor-solid phase support from step (c) causing the lysis of said liposomes, without the addition of any membrane lytic molecules, ions, or active complements, and;
    (e) determining the presence of marker compound released by the liposomes in step (d).

2. The immunoassay of claim 1 wherein step (e) further comprises quantifying the amount of marker compound released and determining the amount of analyte present in the test fluid.

3. The immunoassay of claim 1 wherein said analyte of interest is an antigen.

4. The immunoassay of claim 1 wherein said analyte of interest is an enzyme.

5. The immunoassay of claim 1 wherein said analyte of interest is a drug.

6. The immunoassay of claim 1 wherein said liposomes are comprised of an $H_{II}$ phase forming lipid and an analyte-lipid complex.

7. An immunoassay kit, useful in the method of claim 1, said kit containing in
(a) a sufficient quantity of reagents suitable for preparing a predetermined ligand-lipid complex;
(b) an $H_{II}$ phase forming lipid;
(c) a marker compound capable of being encapsulated within the interior aqueous phase of liposomes;
(d) analyte standards; or
(e) receptor standards;
said kit requiring the use of no membrane lytic molecules, ions, or active complements for its use.

8. An immunoassay kit, useful in the method of claim 1 for detecting the presence of an analyte in a test sample, said kit containing in combination:
(a) a sufficient quantity of stable liposomes having a marker compound incorporated into the interior aqueous phase thereof, and said analyte incorporated onto the surface membrane thereof, wherein said liposomes are comprised of an $H_{II}$ phase forming lipid and an analyte-lipid complex;
(b) a solid support having bound thereto a sufficient quantity of a receptor for said analyte; and
(c) a standard comprising a known amount of said analyte;
(d) said kit requiring the use of no membrane lytic molecules, ions, or active complement for its operation.

9. The immunoassay of claim 1 wherein said solid phase inert support is glass.

10. The immunoassay of claim 9 wherein said glass support is in the form of beads.

11. The immunoassay of claim 1 wherein said marker compound is a self-quenching fluorescent dye.

12. The immunoassay of claim 11 wherein said self-quenching dye is calcein.

13. The immunoassay of claim 1 wherein said solid phase support is a polymer.

14. The immunoassay of claim 13 wherein said polymer is latex.

15. The immunoassay of claim 14 wherein said latex is in bead form.

16. A system for the detection of a biological analyte of interest useful in the method of claim 1, said system consisting of:
(a) marker material encapsulated within the interior aqueous phase and analyte of interest incorporated onto the surface membrane of liposomes, wherein said liposomes are comprised of an $H_{II}$ phase forming lipid and an analyte-lipid complex; and
(b) a receptor for said analyte, said receptor being bound to a solid phase support;
said system requiring the use of no membrane lytic molecules, ions, or active complement for the detection of said analyte.

17. The system of claim 16, wherein said liposomes are composed of dioleyl phosphatidylethanolamine and an antigen-lipid complex.

18. The system of claim 16, wherein said analyte of interest is an antigen.

19. The system of claim 18, wherein said receptor is an antibody for said antigen.

20. The system of claim 16, wherein said solid phase support is glass.

21. The system of claim 20, wherein said glass support is in the form of beads.

22. An immunoassay for detecting or quantifying an analyte of interest in a test fluid, said immunoassay comprising:
(a) forming liposomes having the receptor for the analyte of interest incorporated onto the surface membrane thereof and a marker compound incorporated in the interior aqueous phase thereof;
(b) providing a solid phase inert support having attached thereto the analyte of interest;
(c) mixing said test fluid with the liposomes of step (a) for sufficient time to react with the binding sites on said liposomes with any analyte of interest present in said test fluid;
(d) mixing said reacted liposomes from step (c) with said solid phase bound analyte of step (b) causing the lysis of said liposomes, without the addition of any membrane lytic molecules, ions, or active complement, and;
(e) determining the presence of marker compound released by the liposomes in step (d).

23. The immunoassay of claim 22, wherein step (e) further comprises quantifying the amount of marker compound released and determining the amount of analyte present in the test fluid.

24. The immunoassay of claim 22, wherein said liposomes are comprised of a mixture of an $H_{II}$ phase forming lipid and a receptor or a receptor-lipid complex.

25. The immunoassay of claim 22, wherein said solid phase support is glass.

26. The immunoassay of claim 22, wherein said solid phase support is a polymer.

27. An immunoassay kit, useful in the method of claim 22 for detecting the presence of an analyte in a test sample, said kit containing in combination:
(a) a sufficient quantity of stable liposomes having a marker compound incorporated into the interior aqueous phase thereof, and a receptor for the analyte of interest incorporated onto the surface membrane thereof, wherein said liposomes are comprised of a mixture of an $H_{II}$ phase forming lipid and a receptor or receptor-lipid complex;
(b) a solid support having a sufficient quantity of said analyte of interest bound thereto; and
(c) a standard comprising a known amount of said analyte;
said kit requiring the use of no membrane lytic molecules, ions, or active complement for its operation.

28. The immunoassay of claim 22, wherein said analyte of interest is an antibody.

29. The immunoassay of claim 28, wherein said receptor is an antigen.

30. The immunoassay of claim 22, wherein said marker compound is a self-quenching fluorescent dye.

31. The immunoassay of claim 30, wherein said self-quenching dye is calcein.

32. A system for the detection of an analyte of interest, using the method of claim 22, which system comprises:
(a) a marker material encapsulated in the interior aqueous phase and a sufficient quantity of a receptor for the analyte of interest incorporated onto the surface membrane of liposomes, wherein said liposomes are comprised of a mixture of an $H_{II}$ phase forming lipid and a receptor or a receptor-lipid complex; and (b) a sufficient quantity of analyte of interest bound to a solid phase support;

said system requiring the use of no membrane lytic molecules, ions, or active complement for the detection of said analyte.

33. The system of claim 32, wherein said liposomes are composed of dioleyl phosphatidylethanolamine and and a receptor or a receptor-lipid complex.

34. The system of claim 32, wherein the analyte of interest is an antibody.

35. The system of claim 34, wherein the receptor for the analyte of interest is an antigen.

36. The system of claim 32, wherein said solid phase support is glass.

37. The system of claim 36, wherein said glass support is in the form of beads.

38. The immunoassay of claim 6 or 24, wherein said $H_{II}$ phase forming lipid is an unsaturated phosphatidylethanolamine.

39. The immunoassay of claim 38, wherein said unsaturated phosphatidylethanolamine is selected from the group consisting of dioleyl phosphatidylethanolamine and egg phosphatidylethanolamine.

* * * * *